United States Patent [19]

Miller

[11] Patent Number: 4,725,229
[45] Date of Patent: Feb. 16, 1988

[54] ORTHODONTIC BRACKET
[75] Inventor: Frank R. Miller, Glendora, Calif.
[73] Assignee: Ormco Corporation, Glendora, Calif.
[21] Appl. No.: 875,722
[22] Filed: Jun. 18, 1986
[51] Int. Cl.[4] .............................. A61C 7/00
[52] U.S. Cl. ...................................... 433/11
[58] Field of Search ...................... 433/11, 15

[56] References Cited
U.S. PATENT DOCUMENTS 2,548,864  4/1951  Brusse ............................... 433/11
4,037,324  7/1977  Andreasen ........................ 433/24
4,443,190  4/1984  Kurz .................................. 433/15

Primary Examiner—Robert Peshock
Attorney, Agent, or Firm—Marjama & Pincelli

[57] ABSTRACT

An orthodontic bracket in which the archwire is locked in place by a resilient locking loop member which snaps into and out of engagement over the bracket. The locking loop member is a nickel-titanium wire of high resilience and shape memory which not only locks in the archwire but imparts force against it as a function of the shape memory of the locking loop member.

5 Claims, 13 Drawing Figures

ORTHODONTIC BRACKET

BACKGROUND OF THE INVENTION

The present invention relates to an orthodontic bracket. More particularly, the orthodontic bracket of this invention comprises a bracket body with a mesial-distal slot for the reception of an archwire, and a resilient locking loop member which has a closed position for retaining the archwire in the bracket slot and an open position to allow the archwire to be removed from the bracket slot or inserted into the bracket slot.

Orthodontic archwires are generally made of resilient wire and have a shape and form of a smooth flowing arch which approximates the arch form of the labial surfaces of normal teeth in a normal dental arch.

The archwire is inserted into brackets, which are fixed to the teeth, and then locked into the brackets by various means. The most widely used means of locking the archwire into brackets is to use elastomer "O" rings and/or soft temper stainless steel ligature tie wires. Placing and removing the "O" rings and ligature wires is a time-consuming and tedious task. Elastomer "O" rings loose their elasticity in a very short period of time in the mouth. When this happens, the forces they originally produced to help the archwire straighten the teeth are no longer present.

The new bracket described herein will save valuable time. To tie an archwire into a slot with stainless steel ligature wire, and later remove the ties, takes approximately 30 seconds per tooth. "O" rings require approximately 15 seconds per tooth. To lock and unlock the bracket of the invention will take approximately 5 seconds per tooth. The average orthodontic case will use these brackets on 18 teeth. Therefore each routine of insertion and removal, by the respective methods, requires the following comparative times:

| Ligature Wire | Time to Place and Remove Archwire 18 × 30 Seconds = | 9 Minutes |
|---|---|---|
| "O" Ring | Time to Place and Remove Archwire 18 × 15 Seconds = | 4.5 Minutes |
| This Invention | Time to Place and Remove Archwire 18 × 5 Seconds = | 1.5 Minutes |

The average orthodontic case requires 10 archwire changes or adjustments for each arch (upper and lower), or 20 in-and-out routines. Therefore:

| Ligature Wire | Time | 180 Minutes |
|---|---|---|
| "O" Ring | Time | 90 Minutes |
| This Invention | Time | 30 Minutes |

These routines typically take place over a two year period.

A typical orthodontic treatment requires a series of archwire changes during the course of treatment. At the beginning of treatment the teeth are in their most extreme malpositions. This requires the maximum distortion of the archwire to get working engagement in the bracket slot; therefore, cases are typically started with small diameter, very resilient archwires. As the teeth slowly move, larger and larger diameter archwires replace the smaller archwires. As the case progresses further, round wires are replaced with square or rectangular archwires. The final finishing archwire is usually rectangular in cross section and of a size that fills up the bracket slot with only about 0.002" freedom of movement in the bracket slot. This large finishing archwire is extremely stiff compared to the archwires used earlier in the treatment and is used chiefly to hold the teeth in a solid passive position until the roots of the teeth become stable with the supporting skeletal structure.

SUMMARY OF THE INVENTION

It is an object of this invention to provide an orthodontic bracket permitting substantial savings in time required for repeated openings and closings for removal and adjustments of the associated archwire.

Another object is to provide a bracket in which the archwire locking member produces active forces on the teeth, as compared to prior art ligature wires and O-rings which are relatively passive.

Another object is to provide a bracket which is substantially smaller, and therefore more aesthetic, than corresponding brackets of the prior art.

Another object is to provide a bracket and locking member requiring no special tools for its closing and opening.

Another object is to provide a bracket and locking member which eliminates the use of "O" Rings or ligature wires and the attendant costs of their repeated removal and replacement.

Other objects, advantages, and features will become apparent from the following more detailed description, given in connection with the accompanying drawing.

Briefly, the present invention may be summarized as an orthodontic bracket having a body with an archwire slot and a hook protruding vertically from the body, upwardly or downwardly from the archwire slot. A closed-curved or looped locking member is hinged to the body and swings over the archwire slot and the archwire seated in it, to snap over the hook. The locking member is of a super-elastic shape-memory material such as Nitinol, a nickel-titanium alloy, which provides active tooth-moving forces against the archwire.

DRAWING

DESCRIPTION

Figure 1:
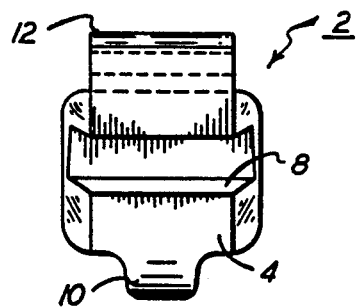
FIG. 1 is a front view of an orthodontic bracket according to the invention.
Figure 3:
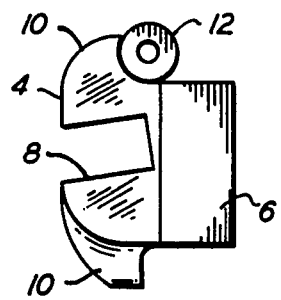
FIG. 3 is a side view from the right side of FIG. 1.
Figure 2:
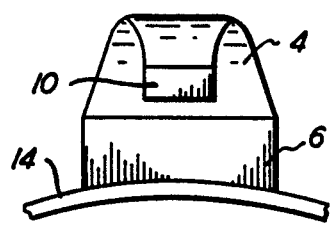
FIG. 2 is a bottom view, looking up at the bracket of FIG. 1.

Referring to the drawing, FIGS. 1-3 show front, bottom and side views of an orthodontic bracket according to this invention. The bracket shown is a lower anterior bracket. For the sake of clarity, this description will be limited to this lower anterior bracket. Brackets for other lower teeth or for the upper teeth may differ in configuration, but such differences are not material here; the inventive concept is common to all such bracket configurations.

Figure 5:
FIG. 5 is a front view of a detail from FIG. 1.
Figure 6:
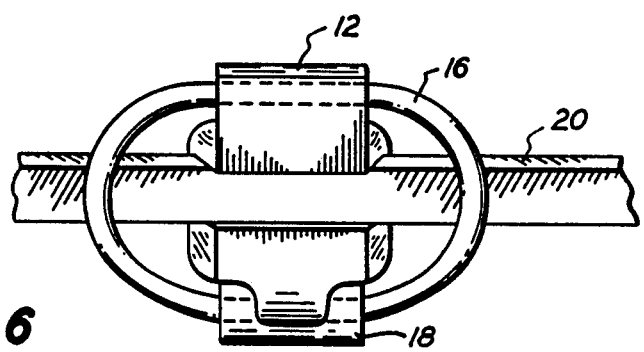
FIG. 6 is a front view of the bracket of FIG. 1, complete with locking loop member in its closed position over an archwire.

The bracket, generally indicated at 2, includes a body 4 having a base portion 6 and a transverse archwire slot 8. The lower portion of the body, forward of the base 6, includes a downward hook 10. A hollow cylindrical tube 12 is fixed to the upper portion of the body 4, the central aperture of tube 12 extending parallel with the archwire slot. Tube 12 is also shown separately in FIG. 5. A mounting pad 14 is fixed to the bottom of the bracket base 6, configured to conform to the curved surface of a tooth.

Figure 4:
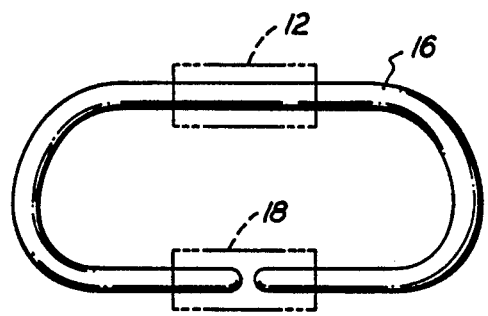
FIG. 4 is a front view of a locking loop member.

FIG. 4 shows a locking loop member 16 which is a substantially closed curve or loop of a resilient wire. The preferred material for locking loop 16 is a nickel-titanium alloy which is a super-elastic shape-memory material. The locking loop 16 is fit through the aperture of tube 12 which is fixed to the bracket body. The fixed tube 12 is represented in phantom on the locking loop in FIG. 4. A second tube 18, similar to tube 12, is mounted over the free ends of locking loop 16, also as represented in phantom in FIG. 4. Tube 18 is tightly crimped around the ends of locking loop 16 to form a closed loop. Locking loop 16 is rotatable or hinged within the fixed tube 12.

Figure 7:
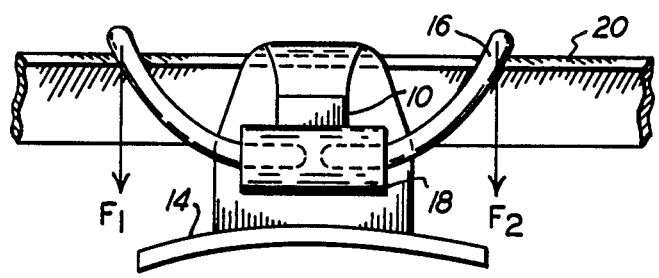
FIG. 7 is a bottom view, looking up at the bracket of FIG. 6.
Figure 8:
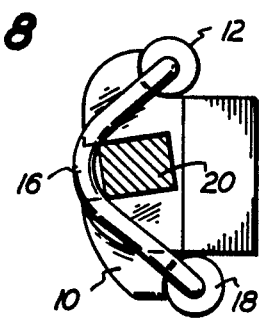
FIG. 8 is a side view from the right side of FIG. 6.
Figure 9:
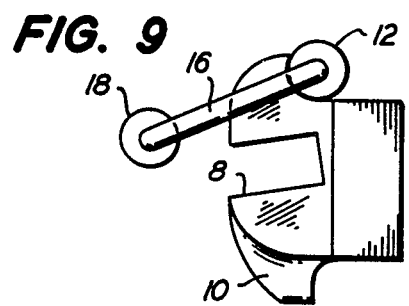
FIG. 9 is a side view from the right side of FIG. 6 showing the bracket in its open condition.

FIGS. 6-9 show the above-described bracket assembly in working relationship relative to an archwire 20. With the bracket in its open position (FIG. 9), the archwire can be inserted in or removed from the archwire slot 8. When the archwire is in place, the free end of locking loop 16 and tube 18 are pulled over it and over the bracket hook 10, into the locking position as best shown in FIG. 8. The resilience of locking loop 16 permits the tube 18 to slide over the hook 10 whereupon the tube 18 is pulled back into its locked position against the hook by the shape memory of loop 16. No special tool is required to open and close this device.

Figure 10:
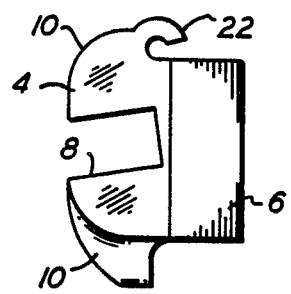
FIG. 10 is a side view of a bracket according to another embodiment of this invention.
Figure 11:
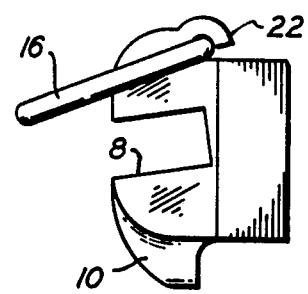
FIG. 11 is a side view of the bracket of FIG. 10, further including a locking loop member in its open position.

FIGS. 10 and 11 show a modified embodiment of the bracket of this invention. The same numerals represent the same elements described in connection with the previously described embodiment, particularly FIGS. 3 and 9. The difference is that in this FIG. 10, 11 embodiment, there is no separate fixed tube 12, but instead a deformable lip or hook 22. The locking loop member 16 is placed behind this lip and the lip thereupon crimped over the loop. The crimp can be either tight against the loop or loose, the essential thing being that the loop is captive behind the crimped lip 22. The loop can then be swung over the archwire slot 8 and snapped over the bracket hook 10 to enclose an archwire as described in connection with the first embodiment.

Figure 12:
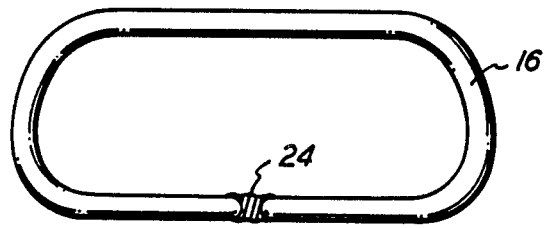
FIG. 12 is a front view of a modified locking loop member.
Figure 13:
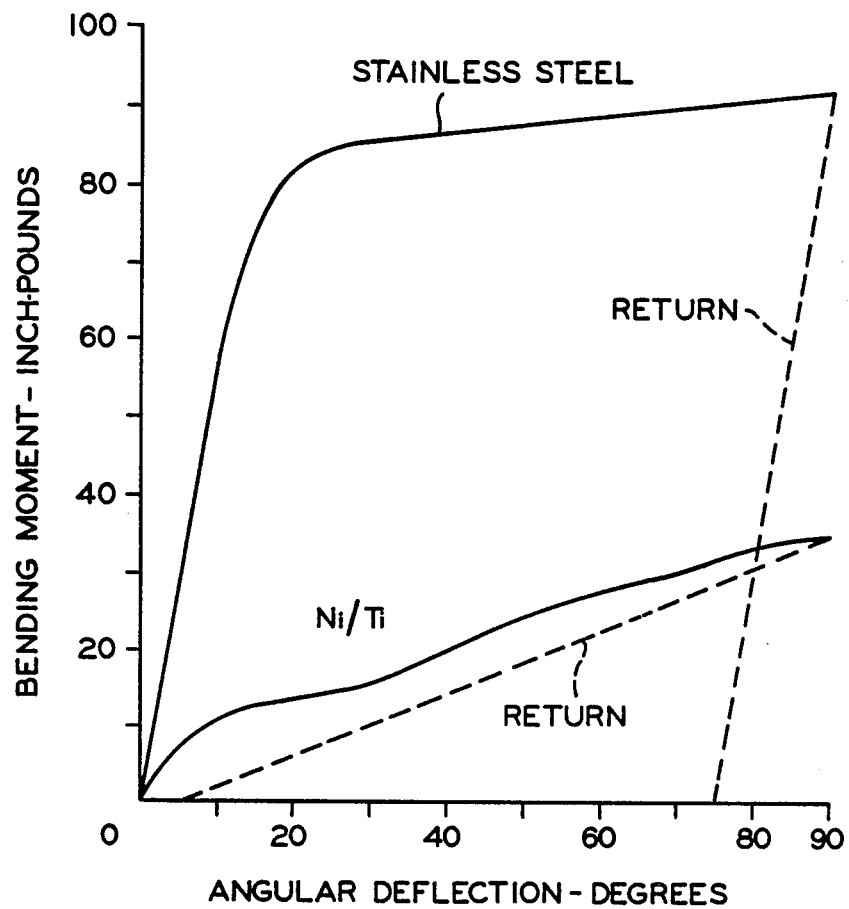
FIG. 13 is a graph comparing the resilience of nickel-titanium alloy with that of stainless steel.

As shown in FIG. 12, the locking loop can be closed by a weld 24 instead of the tube 18 shown in FIG. 4.

The nickel-titanium alloy of which the locking loop 16 is composed provides special advantages. It has greatly superior elasticity and can be bent through large deflections without yield and permanent distortion. It also has shape memory.

a. Elasticity—The locking loop can be distorted and manipulated to a much greater extent than any other known spring material without taking a permanent set or change in shape from its pre-determined memory shape. Other known spring materials such as stainless steel spring temper wire, 300 series, or precipitation hardening stainless steel material or music wire, or any other of the most resilient spring materials are not suitable for use in this invention. They will exceed their elastic limit and take a permanent set when deflected to the extent required here (see wire comparison graph, FIG. 10). FIG. 10 dramatically demonstrates the superiority of the super-elastic nickel-titanium alloy over stainless steel for use in this invention. As demonstrated in FIG. 10, a sample of stainless steel when deflected 90° returns to a permanent set of 75°. In other words, it "springs" back only 15° of the 90°. A similarly sized wire of nickel-titanium alloy (55% nickel–45% titanium) deflected 90° returns to a set of only 6°, i.e. an 84° spring-back. It is this superior resilience which imparts constant forces on the archwire-bracket combinations (see FIG. 7).

b. Shape memory—The shape of the locking member is set in memory of the wire by holding the wire in a fixture and then heat treating the wire in a furnace and then cooling to room temperature. The shaped part is then removed from the fixture and assembled to the bracket. Thus, the locking loop has a pre-determined memory built into it, so that it will always exert force on the archwire, regardless of the size of archwire, tending to seat the archwire completely into the bottom of the bracket slot. The seating forces urged on the archwire by the locking loop are represented in FIG. 7 as F1 and F2. By comparison to these constant forces, elastomeric "O" rings lose their elasticity after a few days so that they no longer produce adequate force. Stainless steel ligature wires also loosen somewhat after a few days in the mouth and allow some degree of looseness of the archwire in the slot. Furthermore, these ties produce no force on their own and they are time consuming to place and remove. A tooth will rotate along its long axis most efficiently if a constant force is present regardless of size of archwire. This constant force in a rotation mode is probably a more valuable feature of this invention than the time saving improvement previously discussed.

An additional advantage to the new bracket is that the overall size of the bracket can be smaller than conventional brackets. Smaller size has the attendent advantages of being more aesthetic, more comfortable to the patient, and more hygienic.

Another advantage is that there is no need to use special tools to open and close the bracket locking loop. Any fine tip dental explorer instrument will suffice to open the bracket. The finger alone can close it.

A further advantage is that the cost of "O" rings and/or ligature wires and their repeated replacement is eliminated.

The most relevant prior art that I know of is U.S. Pat. No. 4,149,314 issued Apr. 17, 1979 to Nonnenmann and U.S. Pat. No. 4,037,324 issued July 26, 1977 to Andreasen.

Nonnenmann discloses an orthodontic bracket with a pivotal wire clasp or fastener. The wire clasp is of stainless steel and is not intended as a resilient, force-imparting spring member. It is apparently a stiff rod-like clasp. This is evidenced by the orientation of the elongated slots in which it fits (which would not be necessary if the clasp were resilient) and also by the fact that the patent speaks of providing auxiliary springs for applying torque or rotational forces where required.

Andreasen discloses the use of Nitinol, a nickel-titanium alloy, for orthodontic archwires. There is, however, no suggestion in Andreasen of the use of this material for interaction between archwire and bracket as evidenced by the conventional ligature tie wires shown in the Andreasen patent.

By comparison to this prior art, the present invention makes use of a nickel-titanium alloy for a bracket locking loop which has both super-elasticity and shape-memory to provide the advantages described.

What is claimed is:

1. An orthodontic bracket including:
    a body defining an archwire slot and including a hook on said body on one side of said body along said archwire slot, said hook having an outer surface and an inner surface,
    a resilient locking loop member mounted to said body on the portion thereof opposite said hook for movement between open and closed positions over said archwire slot, said locking loop member adapted to slide over the outer surface of said hook so as to resiliently snap over said hook and be pulled against said inner surface of said hook to its closed position,
    said locking loop member being of a super-elastic and shape-memory material whereby it is deformable to snap into and out of its closed position and imparts force on an archwire when in its closed position relative thereto.

2. An orthodontic bracket as defined in claim 1 in which said locking loop is of nickel-titanium alloy.

3. An orthodontic bracket as defined in claim 1 further including a tubular member surrounding the free portion of said locking loop for locking engagement with said hook.

4. An orthodontic bracket as defined in claim 1 in which said locking loop member is pivotally mounted to said body.

5. An orthodontic bracket as defined in claim 1 in which said locking loop member is mounted to said body by means of a deformable lip on said body which is crimped over said locking loop.

* * * * *